United States Patent [19]

Inoue

[11] 4,200,089
[45] Apr. 29, 1980

[54] MOUTH CORNER SPREADER

[75] Inventor: Masaomi Inoue, Tokyo, Japan

[73] Assignee: Inoue Attachment Kabushiki Kaisha, Tokyo, Japan

[21] Appl. No.: 895,842

[22] Filed: Apr. 13, 1978

[51] Int. Cl.² .............................................. A61B 1/24
[52] U.S. Cl. ................................................... 128/12
[58] Field of Search ............................... 128/3, 12–15, 128/17–20, 341, 345, 242, 244; 32/34–36

[56] References Cited

U.S. PATENT DOCUMENTS

| | | | |
|---|---|---|---|
| 3,916,880 | 11/1975 | Schroer | 128/12 |
| 3,938,508 | 2/1976 | Buckner | 128/12 X |
| 4,002,162 | 1/1977 | Weisser | 128/15 X |
| 4,019,255 | 4/1977 | Cohen et al. | 128/12 X |

*Primary Examiner*—Robert W. Michell
*Assistant Examiner*—Jeffrey W. Tayon
*Attorney, Agent, or Firm*—Marshall & Yeasting

[57] ABSTRACT

A mouth corner spreader used for spreading both corners of the mouth for facilitating medical examination, treatment, photographing or other works in the mouth. The device comprises a pair of hook structures arranged in opposed relation to each other and designed to fit to the mouth corners, each of said hook structures consisting of a substantially C-shaped external portion, a substantially C-shaped internal portion provided spaced-apart from said external portion and a joining portion joining said external and internal portions along the inside edges of the C-shaped portions, and a substantially U-shaped elastic spring arm connecting said pair of hook structures.

1 Claim, 5 Drawing Figures ial portion 2 and a substantially C-shaped internal portion 3 provided spaced-apart from said external portion 2 on the opposite side thereof and slightly wider than the latter. Said both external and internal portions 2 and 3 are joined by an arcuate portion 4 along the inside edges of the respective C-shaped portions.

MOUTH CORNER SPREADER

BACKGROUND OF THE INVENTION

1. Field of the Invention

This invention relates to a mouth corner spreader used for spreading out the mouth corners at both ends of the lips for facilitating medical examination, treatment, photographing or other works in the mouth.

2. Description of the Prior Art

Among the conventional mouth corner spreading devices is known a type in which hooks are provided at the ends of the handle bars, and for opening the mouth corners by using such device, said hooks are attached to the mouth corners at both ends of the lips and an assistant pulls the handle bars to the right and left with his both hands. This type of mouth corner spreader, however, has the defect that an assistant is required for holding and operating the spreader, beside the person who makes the examination, treatment, photographing, etc., in the mouth.

There is also known another type of mouth corner spreader in which a spring arm is inserted into the mouth and the hooks are fastly attached to the mouth corners at both ends of the lips for effective positive spread-out of the mouth corners. This type of device still has some serious defects. That is, the spring arm which is inserted deed into the mouth in use of the spreader is obstructive to the prosecution of work such as examination, treatment, photographing, etc., in the mouth. Also, the presence of the spring arm in the mouth would give an unpleasant feeling of strangeness to the patient.

SUMMARY OF THE INVENTION

An object of this invention is to provide a mouth corner spreader which makes it possible to perform the medical examination, treatment, photographing or other works in the mouth without necessitating any assistant who has been required in use of the conventional devices for pressing the hook portions of the device against the mouth corners at both ends of the lips.

Another object of this invention is to provide a mouth corner spreader which unnecessitates insertion of a spring arm into the mouth for spreading out the two hooks at the mouth corners to thereby eliminate any risk of impediment thereof to the operation such as examination, treatment, photographing, etc., in the mouth.

Still another object of this invention is to provide a mouth corner spreader in which a spring arm adapted to press the hook portions against the mouth corners at both ends of the lips is substantially U-shaped in general configuration and so arranged that, in use of the device, said arm will be positioned at the jaw portion outside the mouth of the patient, thus allowing easy fitting or removal of the hook portions to or from the mouth corners by compressing or expanding said substantially U-shaped spring arm.

A further object of this invention is to provide a mouth corner spreader in which the spring arm adapted to spread out the two hook portions sidewise is substantially U-shaped and supported by an elastic member so that the same spreader can be used for both child and adult patients.

In order to implement the above-said objects, there is provided according to this invention an improved construction of a mouth corner spreader comprising a pair of hook structures provided in opposed relation to each other and designed to conform to the corners of the mouth, each of said hook structures consisting of a substantially C-shaped external portion, a substantially C-shaped internal portion provided spaced-apart from said external portion on the opposite side thereof and a joining portion which joins said external and internal portions along the inside edges of the respective C-shaped portions, and a substantially U-shaped spring arm connected to the lower ends of the external portions of said respective hook structures.

DESCRIPTION OF PREFERRED EMBODIMENT

Figure 1:
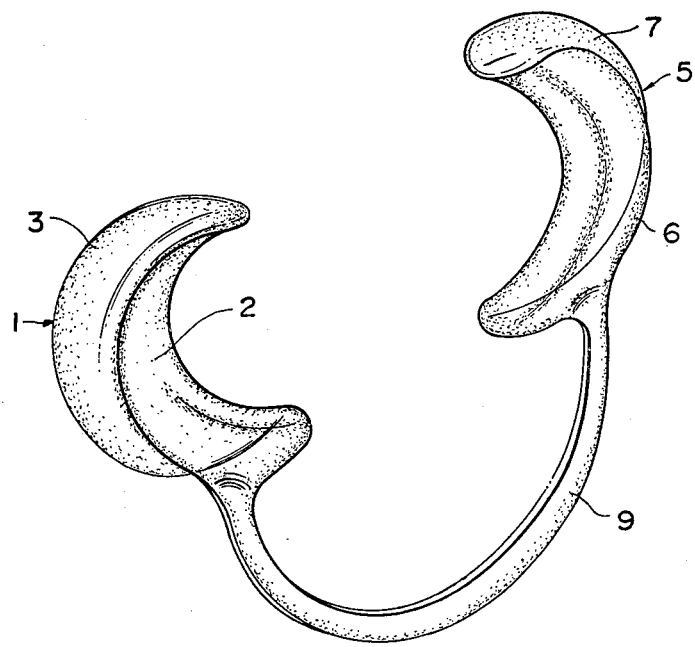
FIG. 1 is a perspective view of a mouth corner spreader in an embodiment of this invention.
Figure 2:
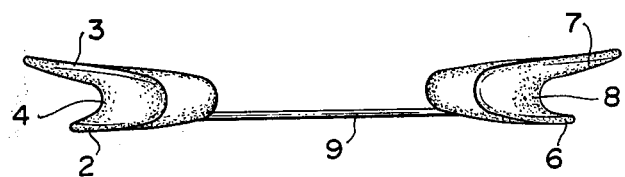
FIG. 2 is a plane view thereof.
Figure 3:
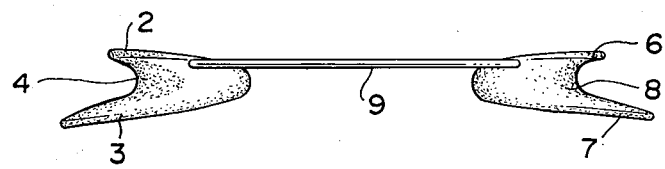
FIG. 3 is a bottom view thereof.
Figure 4:
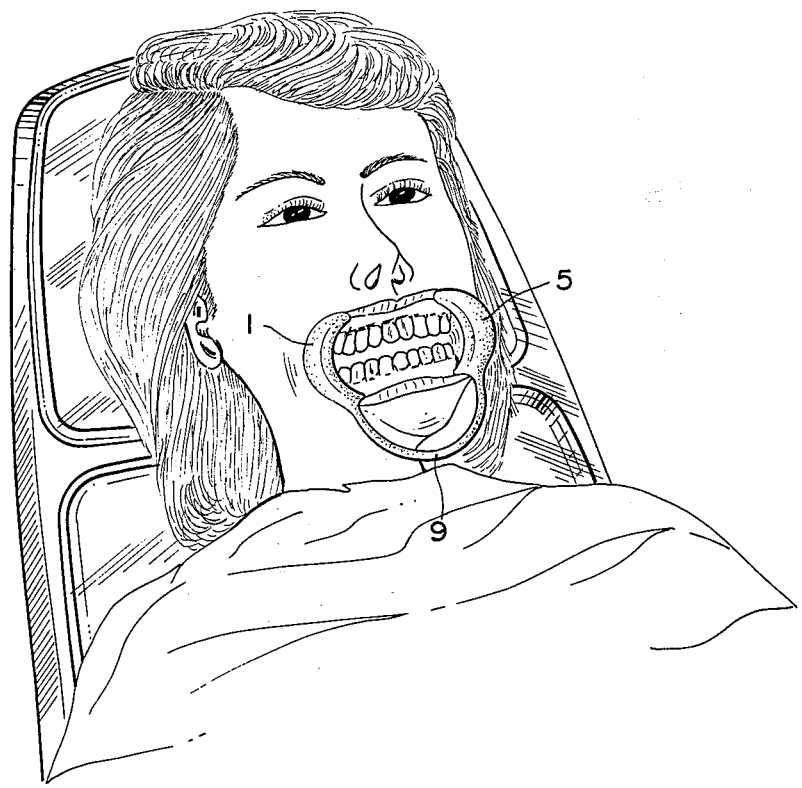
FIG. 4 is a front view of the above mouth corner spreader, showing a mode of use thereof.
Figure 5:
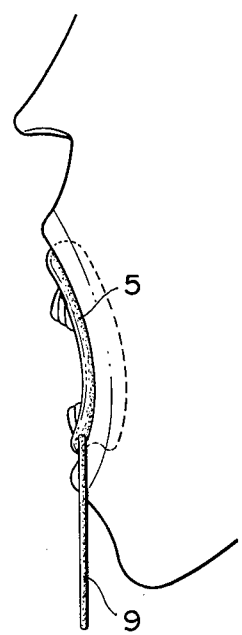
FIG. 5 is a side view of the above spreader in a mode of use.

The present invention is now described in detail by way of an embodiment thereof with reference to the accompanying drawings.

It will be seen that there are provided a pair of mouth corner hooks 1 and 5 adapted to fit to the respective mouth corners and spread them sidewise. The hook 1 is designed to fit to the left corner of the mouth to spread it leftwise and consists of a substantially C-shaped external portion 2 and a substantially C-shaped internal portion 3 provided spaced-apart from said external portion 2 on the opposite side thereof and slightly wider than the latter. Said both external and internal portions 2 and 3 are joined by an arcuate portion 4 along the inside edges of the respective C-shaped portions.

The hook 5 is adapted to fit to the right corner of the mouth to spread it rightwise and consists of a substantially C-shaped external portion 6 and a substantially C-shaped internal portion 7 provided spaced-apart from the external portion 6 on the opposite side thereof and slightly wider than the latter, said both external and internal portions being joined by an arcuate portion 8 along the inside edges of the respective C-shaped portions.

Said both hooks 1 and 5 are arranged in opposition to each other so that they fit to the mouth corners at the right and left ends of the lips, and are connected by a spring arm 9 which is substantially U-shaped in general configuration and rectangular in sectional shape. Said spring arm 9 connects at its both ends to the lower parts of the external portions 2 and 6 of the respective hooks 1 and 5 and is arranged substantially on a same plane as said external portions 2 and 6.

The mouth corner hooks 1, 5 and spring arm 9 may be made of a synthetic resin material such as polycarbonate or nylon which is elastic and has sufficient heat resistance to withstand boiling water disinfection and sufficient chemical resistance to withstand chemical disinfection. Other materials having sufficient elasticity and heat and chemical resistance, such as methyl alloys, are also usable.

The sectional shape of the spring arm 9 needn't be rectangular; it may be oval or circular.

In use of the spreader of this invention, first the spring arm 9 is gripped and compressed to narrow down the distance between the hooks 1 and 5 and then the hooks are placed into the mouth by positioning the internal portions 3, 7 inside of the mouth corners at both ends of the lips while positioning the external portions 2, 6 on the outside of the mouth corners, and then the mouth corners are spread out by dint of the joining portions 4, 8 to create a situation convenient for performing medical examination, treatment, photographing or other work in the mouth. In this case, the hooks 1, 5 fitted to the right and left corners of the mouth dont't press the lips locally but are able to let the mouth corners spread out in an almost natural way. Also, proper elasticity of the spring arm 9 accommodates adaptation of the device to the childern's small mouths as well as to the adult's ones.

What is claimed is:

1. A mouth corner spreader comprising a pair of hooks arranged in opposed relation to each other, designed to fit to the mouth corners, each of said hooks consisting of a substantially C-shaped external portion, a substantially C-shaped internal portion spaced-apart from said external portion, said internal portion being slightly wider than said external portion to extend outwardly beyond the external C-shaped portion, and an arcuate portion which joins said both external and internal portions along the inside edges of the respective C-shaped portions, and a substantially U-shaped spring arm connected to the lower parts of the external portions of said both hooks and extending downwardly and substantially in the same vertical plane as said external portions of both hooks and positioned outside the mouth when the hooks are in place, the C-shaped internal portions which extend beyond the C-shaped external portions having a tapered surface flaring away from said external portions and engaging the inside of the mouth adjacent the corners.

* * * * *